United States Patent
Slabaugh et al.

(10) Patent No.: US 12,220,028 B1
(45) Date of Patent: Feb. 11, 2025

(54) WATCH BAND WITH WRIST DETECTION

(71) Applicant: Apple Inc., Cupertino, CA (US)

(72) Inventors: Scott W. Slabaugh, Gilroy, CA (US); Osamu Yabe, Mountain View, CA (US)

(73) Assignee: Apple Inc., Cupertino, CA (US)

( * ) Notice: Subject to any disclaimer, the term of this patent is extended or adjusted under 35 U.S.C. 154(b) by 918 days.

(21) Appl. No.: 17/131,460

(22) Filed: Dec. 22, 2020

Related U.S. Application Data (60) Provisional application No. 62/984,733, filed on Mar. 3, 2020.

(51) Int. Cl.
| | | |
|---|---|---|
| A44C 5/00 | (2006.01) | |
| A61B 5/00 | (2006.01) | |
| A61B 5/021 | (2006.01) | |

(52) U.S. Cl.
CPC ............ *A44C 5/0053* (2013.01); *A61B 5/681* (2013.01); *A61B 5/6843* (2013.01); *A61B 5/021* (2013.01)

(58) Field of Classification Search
CPC .... G04G 21/025; A44C 5/0053; A61B 5/021; A61B 5/681; A61B 5/6843
See application file for complete search history.

(56) References Cited

U.S. PATENT DOCUMENTS

| | | | |
|---|---|---|---|
| 9,609,921 B1 | | 4/2017 | Feinstein |
| 9,781,984 B2 | | 10/2017 | Baranski |
| 9,939,784 B1 | | 4/2018 | Berardinelli |
| 10,149,521 B2 | * | 12/2018 | Baranski .............. A44C 5/0069 |
| 10,849,556 B2 | * | 12/2020 | Lumme ................. A61B 5/1118 |
| 11,165,141 B2 | * | 11/2021 | Hsu ........................ H01Q 1/273 |
| 11,540,599 B1 | * | 1/2023 | Yokoyama ........... A44C 27/008 |
| 11,589,815 B1 | * | 2/2023 | Williams ............. A61B 5/7405 |
| 11,602,201 B1 | * | 3/2023 | Slabaugh ............. A44C 5/0069 |
| 11,890,083 B1 | * | 2/2024 | Williams ............. A61B 5/6843 |
| 2018/0271232 A1 | | 9/2018 | Yabe et al. |
| 2019/0341677 A1 | * | 11/2019 | Hsu ........................ A44C 5/0007 |
| 2020/0093378 A1 | * | 3/2020 | Lange ................... A61B 5/0295 |
| 2022/0400961 A1 | * | 12/2022 | Wang .................... A61B 5/0205 |
| 2023/0079679 A1 | * | 3/2023 | Leith ....................... G04G 21/02 368/10 |
| 2024/0074549 A1 | * | 3/2024 | Olmstead ............. A44C 5/2071 |
| 2024/0126219 A1 | * | 4/2024 | Taylor ..................... G06F 3/016 |

FOREIGN PATENT DOCUMENTS

| | | | | |
|---|---|---|---|---|
| EP | 1490925 B1 | * | 3/2008 | ....... G06K 19/07762 |
| WO | WO-2018034159 A1 | * | 2/2018 | ............. G01L 1/146 |

* cited by examiner

*Primary Examiner* — Octavia Hollington
(74) *Attorney, Agent, or Firm* — BAKERHOSTETLER (57) ABSTRACT

Characteristics of a watch band can change when placed in different configurations, and each of these characteristics can be correlated with each of the various configurations. The characteristics can be measured to detect in which of the various configurations the watch band is in. For example, the watch band can include a conductive trace that changes its resistance when the watch band changes its configuration. For example, the resistance can change based on stretching of the watch band, bending of the watch band, and/or securement and release of an engagement element. The watch or another device can perform one or more operations based on the detected characteristic and configuration of the watch band.

19 Claims, 7 Drawing Sheets

WATCH BAND WITH WRIST DETECTION

CROSS-REFERENCE TO RELATED APPLICATION

This application claims the benefit of U.S. Provisional Application No. 62/984,733, entitled "WATCH BAND WITH WRIST DETECTION," filed Mar. 3, 2020, the entirety of which is incorporated herein by reference.

FIELD

The present description relates generally to watch bands, and, more particularly, to watch bands with detection of a user's wrist and/or characteristics thereof.

BACKGROUND

Some electronic devices may be removably attached to a user. For example, a wristwatch or fitness/health tracking device can be attached to a user's wrist by joining free ends of a watch band together.

Proximity sensors are capable of detecting the presence of a target without physical contact. They generally emit electromagnetic radiation, measure the return signal, and identify the location of the target based on the profile of the return signal. Proximity sensors are commonly used on mobile devices such as smartphones to detect accidental touchscreen taps when held to the ear during a call. Portable devices such as wristwatches may also include a proximity sensor that detects whether the watch is "off wrist" and should be turned to a locked state. However, for those users who prefer to wear their watch loosely against their wrist, such a proximity sensor may cause unintentional locking of the watch or other undesired consequences.

Accordingly, it may be beneficial to develop alternate methods or devices to more accurately determine the configuration and/or location of a wearable device relative to the user.

BRIEF DESCRIPTION OF THE DRAWINGS

Certain features of the subject technology are set forth in the appended claims. However, for purpose of explanation, several embodiments of the subject technology are set forth in the following figures.

DETAILED DESCRIPTION

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, it will be clear and apparent to those skilled in the art that the subject technology is not limited to the specific details set forth herein and may be practiced without these specific details. In some instances, well-known structures and components are shown in block diagram form in order to avoid obscuring the concepts of the subject technology.

Embodiments described herein relate to systems and methods for detection of a configuration and/or location of a wearable device relative to a user. It should be appreciated that the various embodiments described herein, as well as functionality, operation, components, and capabilities thereof may be combined with other elements, embodiments, structures and the like, and so any physical, functional, or operational discussion of any element or feature is not intended to be limited solely to a particular embodiment to the exclusion of others.

As noted above, many portable electronic devices may be removably attached to a user. The wearable devices may be any electronic device suitable for contact with a user's skin, e.g., a phone, wristwatch, arm or wristband, headband, or any device where detection of relative surface orientation may be useful. The wearable device may be worn on a wrist, ankle, head, chest, leg, etc., with the use of a band that is flexible and capable of adjustably fitting a user. For example, the watch band may be made from a flexible material or have a structure that allows it to have an adjustable circumference. In some examples, the wearable device is a watch, smart watch, wristwatch, timekeeping device, or other wrist-worn device.

In some examples, a smart watch or a fitness device can be attached to a user's wrist by donning the watch with a watch band and/or joining free ends of a conventional watch band together. In other examples, a clasp or an elasticated band may optionally be used to secure the watch. In another example, a portable audio player may be secured to a user's arm by inserting the player into an armband case. In another example, a heart rate sensor may be attached to a user's chest by a strap.

Although many embodiments are described herein with reference to wrist bands for attaching a wrist-worn electronic device to a user, one may appreciate that other form factors may be favored in other embodiments. In other words, the methods, systems, and techniques described herein with illustrative reference to wrist-worn devices may be equally applied to non-wrist worn devices. For example, in other embodiments, devices may be configured to attach to other limbs or body portions (e.g., necklaces, arm bands, waistbands, ear hooks, finger rings, anklets, toe rings, chest wraps, head bands, etc.). Furthermore, other embodiments described herein may be applied to detect the configuration and/or location of an electronic device with respect to a non-user object such as a charging stand or station.

As noted above, some watches or other wearable devices have a capability to detect the presence of a user or other object to which it is secured. For example, proximity sensors are capable of detecting the presence of a target without physical contact. Portable devices such as wristwatches may use such detections to determine whether the watch is "off wrist" and should be turned to a locked state or provide other functions. However, for those users who prefer to wear their watch loosely against their wrist, such a proximity sensor may cause unintentional locking of the watch or other undesired consequences.

Accordingly, many embodiments described herein relate to systems and methods for detecting the configuration and/or location of a watch and/or watch band with respect to a user or other object. Such detections can be made based on changes in the watch band of the watch. For example, the watch band can have a different length, tension, curvature, securement configuration, or other characteristics when it is on the wrist of the user (i.e., "on-wrist" or "in an on-wrist configuration") relative to when it is off of the wrist of the user (i.e., "off-wrist" or "in an off-wrist configuration").

Characteristics of a watch band can change when placed in different configurations, and each of these characteristics can be correlated with each of the various configurations. The characteristics can be measured to detect in which of the various configurations the watch band is in. For example, the watch band can include a conductive trace that changes its resistance when the watch band changes its configuration. For example, the resistance can change based on stretching of the watch band, bending of the watch band, and/or securement and release of an engagement element.

The watch or another device can perform one or more operations based on the detected characteristic and configuration of the watch band. For example, the watch can respond to a detection by granting or restricting access to one or more features of the watch. By further example, the watch can use a detection to further detect a size of the user's wrist. By further example, the watch can use a detection to further detect a movement, activity, and/or gesture of the user. By further example, the watch can use a detection to further detect a health metric of the user, such as blood pressure.

These and other embodiments are discussed below with reference to FIGS. 1-17. However, those skilled in the art will readily appreciate that the detailed description given herein with respect to these figures is for explanatory purposes only and should not be construed as limiting.

Figure 1:
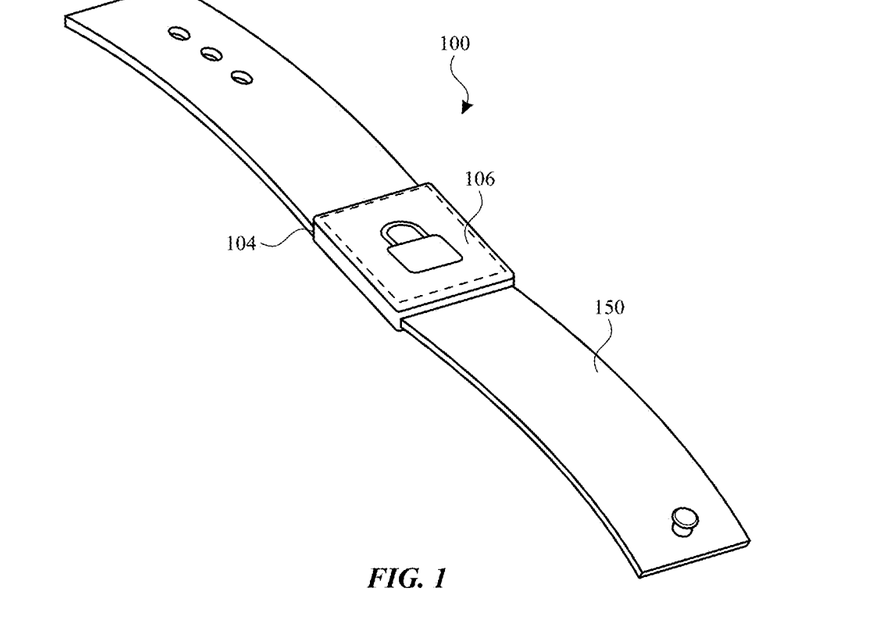
FIG. 1 illustrates a perspective view of a watch, according to some embodiments of the present disclosure.
Figure 2:
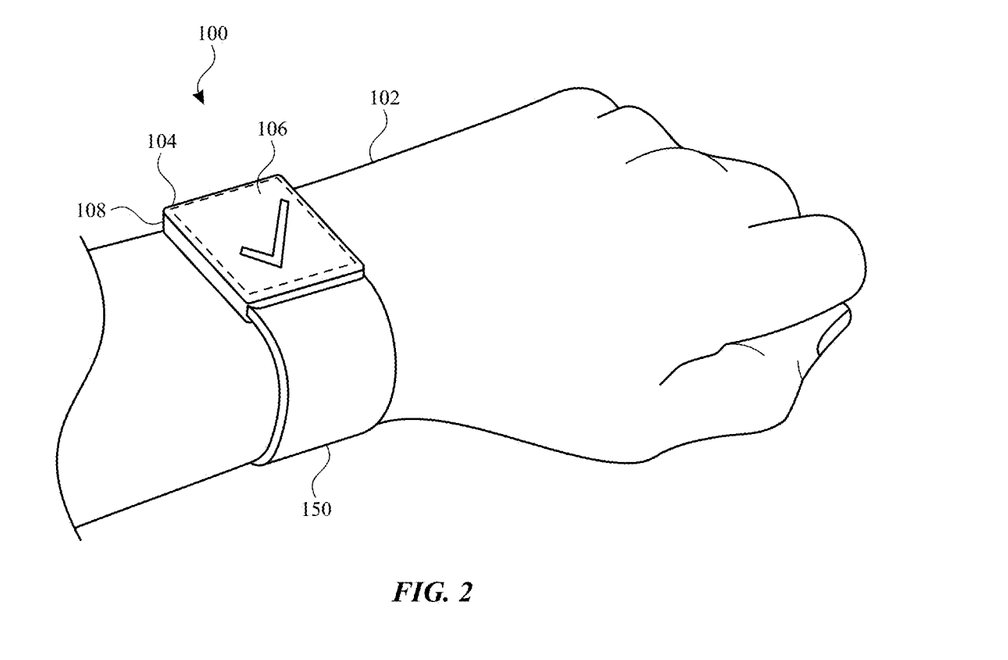
FIG. 2 illustrates a perspective view of a watch on a wrist of a user, according to some embodiments of the present disclosure.

Referring to FIGS. 1 and 2, a watch can be provided in a relaxed off-wrist configuration (FIG. 1) or in an on-wrist configuration by attaching the watch to a wrist of a user (FIG. 2).

FIG. 1 depicts a perspective view of a watch a relaxed off-wrist configuration. In the illustrated embodiment, the watch 100 is implemented as a portable electronic device that is wearable on a wrist. Other embodiments can implement the watch differently. For example, the watch can be a smart phone, a gaming device, a digital music player, a sports accessory device, a medical device, navigation assistant, accessibility device, a device that provides time and/or weather information, a health assistant, and other types of electronic device suitable for attaching to a user.

A watch body 104 of the watch 100 can include a housing 108 and a display 106. The housing 108 can form an outer surface or partial outer surface and protective case for one or more internal components of the watch 100. In the illustrated embodiment, the housing 108 is formed into a substantially rectangular shape, although this configuration is not required and other shapes are possible in other embodiments.

In some examples, the display 106 may incorporate an input device configured to receive user input. The display 106 can be implemented with any suitable technology, including, but not limited to, a multi-touch sensing touch-screen that uses liquid crystal display (LCD) technology, light emitting diode (LED) technology, organic light-emitting display (OLED) technology, organic electroluminescence (OEL) technology, or another type of display technology. In many embodiments, the display 106 can be disposed below a protective cover glass formed from a rigid and scratch resistant material such as ion-implanted glass, laminated glass, or sapphire.

As noted above, the display 106 can incorporate or be disposed proximate to an input sensor. For example, in some embodiments, the display 106 can also include one or more contact sensors to determine the position of one or more contact locations on a top surface of the display 106. In some embodiments, the display 106 can also include one or more force-sensitive elements (not shown) to detect a magnitude of force applied to the top surface of the display 106.

The watch 100 can include within the housing 108 a processor, a memory, a power supply and/or battery, network communications, sensors, display screens, acoustic elements, input/output ports, haptic elements, digital and/or analog circuitry for performing and/or coordinating tasks of the watch 100, and so on. In some examples, the watch 100 can communicate with a separate electronic device via one or more proprietary and/or standardized wired and/or wireless interfaces. For simplicity of illustration, the watch 100 is depicted in FIG. 1 without many of these elements, each of which may be included, partially, optionally, or entirely, within the housing 108.

FIG. 2 depicts a perspective view of the watch 100 in an on-wrist configuration by being attached by the watch band 150 to a user 102. The watch body 104 of the watch 100 can be coupled to the user 102 via a watch band 150 that loops around the user's wrist. The watch band 150 can be formed from a compliant material, or into a compliant structure, that is configured to easily contour to a user's wrist, while retaining stiffness sufficient to maintain the position and orientation of the watch on the user's wrist. The material selected for the watch band 150 may vary from embodiment to embodiment. For example, in certain cases, the watch band 150 can be formed from metal, such as a band formed into a metal mesh. In other embodiments, the watch band 150 can be formed from an organic material such as leather. In further examples, the watch band 150 can be formed from an inorganic material such as nylon. In still further embodiments, materials such as plastic, rubber, or other fibrous, organic, polymeric, or synthetic materials may be used.

In some examples, the watch band 150 can be removably coupled to the housing 108. For example, in certain embodiments, the watch band 150 can be at least partially looped around a watch pin that is configured to insert within lugs extending from the body of the housing 108. In other examples, the watch band 150 can be configured to slide within and be retained by two or more channels within external sidewalls of the housing 108. In other examples, the watch band 150 can be looped through and aperture in the housing 108. In other cases, the watch band 150 can be riveted, screwed, or otherwise attached to the housing 108 via one or more mechanical fasteners. In still further embodiments, additional removable couplings between the watch band 150 and the housing 108 are possible.

In other examples, the watch band 150 can be permanently coupled to the housing 108. For example, in some cases, the watch band 150 may be formed as an integral portion of the housing 108. In other cases, the watch band 150 can be rigidly adhered to the housing 108 via an adhesive. In still further embodiments, the watch band 150 can be welded, soldered, or chemically bonded to the housing 108. In other embodiments, additional permanent couplings between the watch band 150 and the housing 108 are possible.

As noted above, the housing 108 of the watch body 104 may be rigid and can be configured to provide structural support and impact resistance for electronic or mechanical components contained therein. A rigid housing is not necessarily required for all embodiments and, in some examples, the watch 100 can have a housing may be flexible. Furthermore, although watch housings are typically formed to take a rectangular shape, this is not required and other shapes are possible. For example, certain housings may take a circular shape.

In other embodiments, the watch 100 can include one or more sensors (not shown) positioned on a bottom surface of the housing 108. Sensors utilized by the watch 100 can vary from embodiment to embodiment. Suitable sensors can include temperature sensors, electrodermal sensors, blood pressure sensors, heart rate sensors, respiration rate sensors, oxygen saturation sensors, plethysmographic sensors, activity sensors, pedometers, blood glucose sensors, body weight sensors, body fat sensors, blood alcohol sensors, dietary sensors, and so on.

In many cases, sensors such as biometric sensors can collect certain health-related information non-invasively. For example, the watch 100 can include a sensor that is configured to measure changes in (or an amount of) light reflected from a measurement site (e.g., wrist) of the user 102. In one embodiment, the biometric sensor such as a PPG sensor can include a light source for emitting light onto or into the wrist of the user 102 and an optical sensor to detect light exiting the wrist of the user 102. Light from the light source may be scattered, absorbed, and/or reflected throughout the measurement sight as a function of various physiological parameters or characteristics of the user 102. For example, the tissue of the wrist of the user 102 can scatter, absorb, or reflect light emitted by the light source differently depending on various physiological characteristics of the surface and subsurface of the user's wrist.

In many cases a PPG sensor can be used to detect a user's heart rate and blood oxygenation. For example, during each complete heartbeat, a user's subcutaneous tissue can distend and contract, alternatingly increasing and decreasing the light absorption capacity of the measurement site. In these embodiments, the optical sensor of the PPG can collect light exiting the measurement site and generate electrical signals corresponding to the collected light. Thereafter, the electrical signals can be conveyed as raw data to the watch 100, which in turn can process the raw data into health data. The raw data can be based on information about the collected light, such as the chromaticity and/or luminance of the light. In some cases, the health data can be shown on the display 106 as biometric feedback to the user 102.

Depending on the configuration, location, and/or orientation of the watch 100 relative to the user 102, as detected by any of the methods described herein, the watch 100 may perform or prevent one or more operations. For example, if a detected characteristic of the watch band 150 corresponds to a configuration in which the watch 100 is "off-wrist," as illustrated in FIG. 1, then the watch 100 may be turned to a locked (i.e., where a passcode is required to access information on the device) or low power state. By further example, if the detected characteristic of the watch band 150 corresponds to a configuration in which the watch 100 is "on-wrist," as illustrated in FIG. 2, then the watch 100 may be turned to an unlocked state (i.e., where a passcode is not required to access information on the device or is only required once while the on-wrist configuration is maintained). Additionally or alternatively, other operations can be performed based on the detected characteristic, as discussed further herein. In some variations, the resistance characteristics of the watch band may be used to detect whether the watch 100 is "on wrist" or "off wrist," as discussed further herein. Corresponding indications can be output to the user, for example via the display 106.

Figure 3:
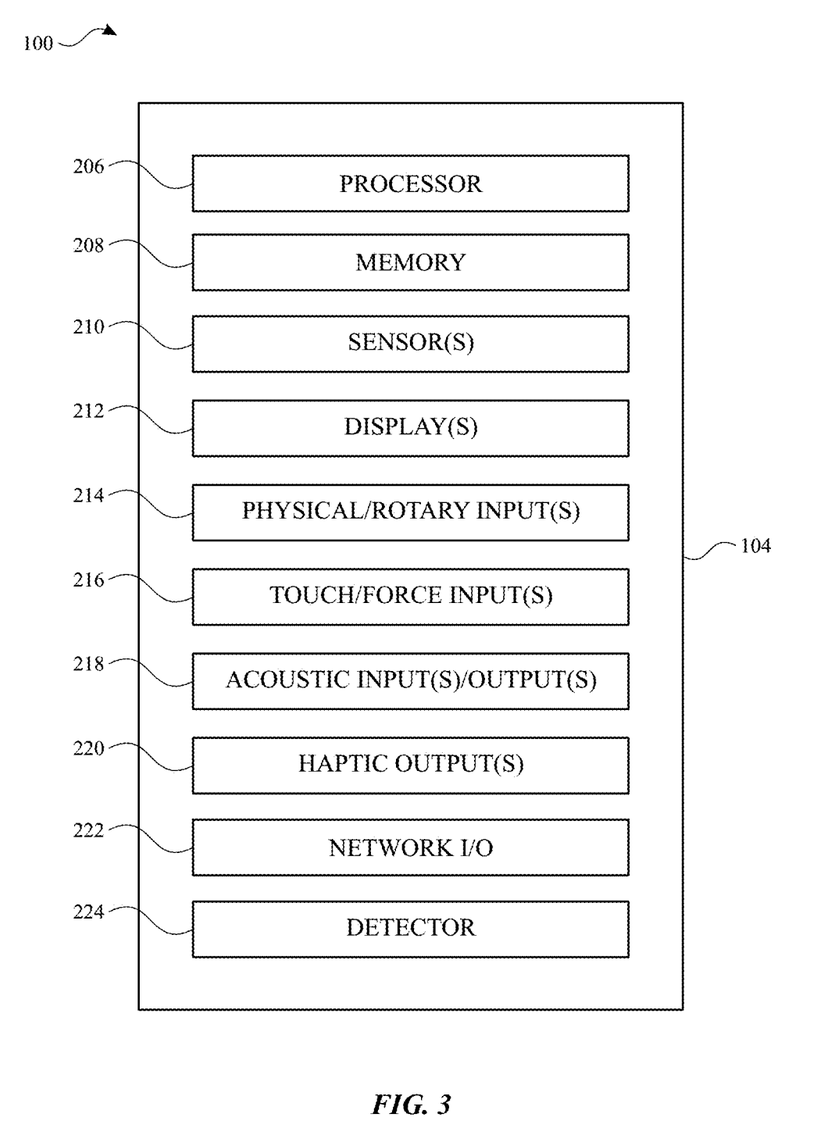
FIG. 3 depicts a simplified block diagram of a watch, according to some embodiments of the present disclosure.

FIG. 3 depicts a simplified block diagram of a watch 100 configured to perform the operations described herein. The watch 100 can one or more processing devices 206, memory 208, one or more input/output (I/O) devices or sensors 210 (e.g., biometric sensors, environmental sensors, etc.), one or more displays 212, one or more power source(s) (not shown), one or more physical and/or rotary input devices 214, one or more touch and/or force input device(s) 216, one or more acoustic input and/or output devices 218, one or more haptic output device(s) 220, one or more a network communication interface(s) 222, and one or more detectors 224. Some embodiments can also include additional components. One or more of these components can be provided on the watch body and/or the watch band of the watch. Appropriate communication connections can be provided between components, including those separated by an interface between the watch body and/or the watch band of the watch 100.

The display 212 may provide an image or video output for the watch 200. The display 212 may also provide an input surface for one or more input devices such as a touch sensing device 216, force sensing device, temperature sensing device, and/or a fingerprint sensor. The display 212 may be any size suitable for inclusion at least partially within the housing of the watch 100 and may be positioned substantially anywhere on the watch 100. In some embodiments, the display 212 can be protected by a cover glass formed from a scratch-resistant material (e.g., sapphire, zirconia, glass, and so on) that may form a substantially continuous external surface with the housing of the watch 100.

The processing device(s) 206 can control or coordinate some or all of the operations of the watch 100. The processing device 206 can communicate, either directly or indirectly with substantially all of the components of the watch 100. For example, a system bus or signal line or other communication mechanisms can provide communication between the processing device 206, the memory 208, the sensor(s) 210, the power source(s), the network communication interface 222, and/or the haptic output device 220.

The one or more processing devices 206 can be implemented as any electronic device capable of processing, receiving, or transmitting data or instructions. For example, the processing device(s) 206 can each be a microprocessor, a central processing unit (CPU), an application-specific integrated circuit (ASIC), a digital signal processor (DSP), or combinations of such devices. As described herein, the term "processing device" is meant to encompass a single processor or processing unit, multiple processors, multiple processing units, or other suitably configured computing element or elements.

The memory 208 can store electronic data that can be used by the watch 100. For example, a memory can store electrical data or content such as, for example, audio and video files, documents and applications, device settings and user preferences, timing and control signals or data for the haptic output device 220, data structures or databases, and so on. The memory 208 can be configured as any type of memory. By way of example only, the memory can be implemented as random access memory, read-only memory, Flash memory, removable memory, or other types of storage elements, or combinations of such devices.

The sensor(s) 210 can transmit and/or receive data to and from a user or another electronic device. The sensor(s) 210 can include a touch sensing input surface such as one or more buttons, one or more microphones or speakers, and/or one or more ports such as a microphone port.

The watch 100 may also include one or more sensors 210 positioned substantially anywhere on the watch 100. The sensor or sensors 210 may be configured to sense substantially any type of characteristic such as, but not limited to, images, pressure, light, touch, force, temperature, position, motion, and so on. For example, the sensor(s) 210 may be an image sensor, a temperature sensor, a light or optical sensor, an atmospheric pressure sensor, a humidity sensor, a magnet, a gyroscope, an accelerometer, and so on. In other examples, the watch 100 may include one or more health sensors. In some examples, the health sensors can be disposed on a bottom surface of the housing of the watch 100.

The power source can be implemented with any device capable of providing energy to the watch 100. For example, the power source can be one or more batteries or rechargeable batteries, or a connection cable that connects the remote control device to another power source such as a wall outlet. In other examples, wireless power can be used.

The network communication interface 222 can facilitate transmission of data to or from other electronic devices across standardized or proprietary protocols. For example, a network communication interface can transmit electronic signals via a wireless and/or wired network connection. Examples of wireless and wired network connections include, but are not limited to, cellular, Wi-Fi, Bluetooth, infrared, and Ethernet.

The haptic output device 220 can be implemented as any suitable device configured to provide force feedback, vibratory feedback, tactile sensations, and the like. For example, in one embodiment, the haptic output device 220 may be implemented as a linear actuator configured to provide a punctuated haptic feedback, such as a tap or a knock.

As noted above, the watch 100 can include a detector 224. In some embodiments, a detector can be an analog, digital, or integrated circuit configured to measure, monitor, probe, or otherwise interact with at least a portion of the watch band for determination of a characteristic thereof. The detector 224 can be or include an ohmmeter and the detected characteristic can be a resistance of at least a portion of the watch band. The detector 224 can communicate with the processor 206 and/or another component and/or device to perform operations based on the characteristic (e.g., resistance) detected by the detector 224. Such operation can include providing output to the user, performing calculations, communicating with other devices, and/or performing additional detections.

Figure 4:
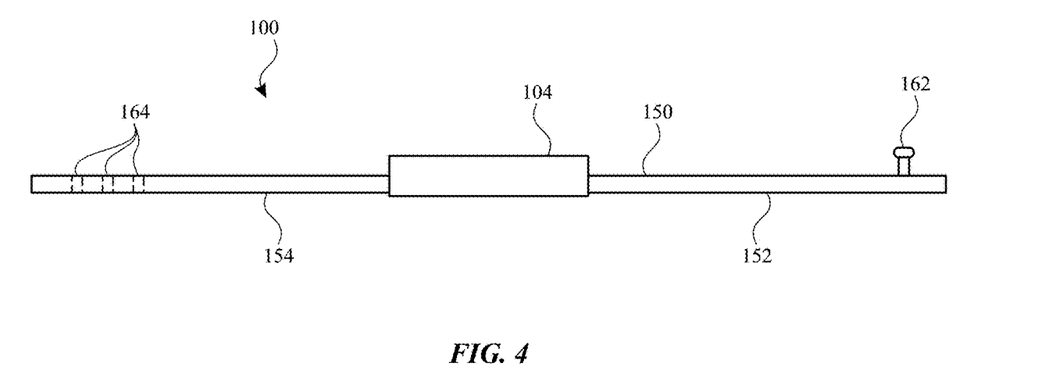
FIG. 4 illustrates a side view of a watch in a relaxed configuration, according to some embodiments of the present disclosure.
Figure 5:
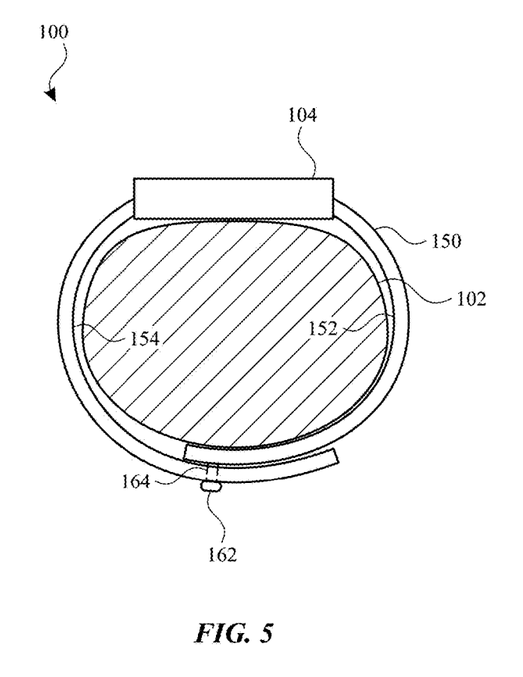
FIG. 5 illustrates a side view of the watch of FIG. 4 in a secured configuration on a wrist of a user, according to some embodiments of the present disclosure.

Referring now to FIGS. 4 and 5, a watch can be provided with an ability to be transitioned between different configurations, such as on-wrist and off-wrist configurations. Changes in the configurations can have corresponding and detectable effects on one or more characteristics of the watch band.

FIG. 4 depicts a side view of a watch in a relaxed off-wrist configuration. As shown in FIG. 4, the watch band 150 can include a first band portion 152 and a second band portion 154. The first band portion 152 can include a first engagement element 162, and the second band portion 154 can include the second engagement element 164.

The first band portion 152 and the second band portion 154 can extend away from each other and/or the watch body 104 while the watch band 150 is in the relaxed off-wrist configuration. Such a configuration can be one in which the watch band 150 is allowed to extend to a preferred position and/or orientation in the absence of external forces. Additionally or alternatively, such a configuration can be one that the watch band 150 assumes when the watch 100 is placed on a flat surface.

As shown in FIG. 5, the watch band 150 can be formed from a compliant material or into a compliant structure that is configured to easily contour to the wrist of the user 102.

The watch band 150 is illustrated as overlapping components to form a closed loop around the wrist of the user 102. In these examples, the first band portion 152 and the second band portion 154 can be affixed together. For example, the first engagement element 162 can engage the second engagement element 164 to secure the first band portion 152 and the second band portion 154 relative to each other. The first engagement element 162 and the second engagement element 164 can engage each other in one or more of a variety of configurations to provide different fits or levels of tightness on the wrist of the user 102.

For example, the first engagement element 162 can include a post or other protruding member that extends away from a portion of the first band portion 152. The second engagement element 164 can be or include one or more openings extending through at least a portion of the second band portion 154. By further example, the first engagement element 162 and the second engagement element 164 can form a buckling clasp. By further example, the first engagement element 162 and the second engagement element 164 can include locks, latches, snaps, screws, clasps, threads, magnets, pins, an interference (e.g., friction) fit, knurl presses, bayoneting, hook and loop fasteners, and/or combinations thereof.

While the watch band 150 is illustrates as having overlapping components, the watch band 150 can alternatively form a single, continuous structure extending from opposing ends of the watch body 104. The watch band 150 can be expanded to don or remove the watch 100 from the wrist of the user 102 and provide sufficient tightness on the wrist of the user 102 to remain in a desired position and orientation.

When transitioning between the relaxed off-wrist configuration and the secured on-wrist configuration, the watch band can undergo a change to at least one characteristic (e.g., resistance) in a manner that is detectable. Such detections can be made as result of a change in the length, engagement state, and/or curvature of the watch band.

In the relaxed off-wrist configuration, as shown in FIG. 4, the watch band 150 can have a first length, for example in which it is not stretched along a longitudinal axis (e.g., allowed to contract longitudinally towards the watch body 104). In the secured on-wrist configuration, as shown in FIG. 5, the watch band 150 can have a second length, different (e.g., greater) than the first length, for example in which it is stretched along the longitudinal axis (e.g., longitudinally away from the watch body 104). The stretching of the watch band 150 along its length can change at least one characteristic (e.g., resistance) of at least a portion of the watch band 150 in a manner that is detectable.

In the relaxed off-wrist configuration, as shown in FIG. 4, the engagement elements 162 and 164 of the watch band 150 can be disengaged and/or separated from each other. In the secured on-wrist configuration, as shown in FIG. 5, the engagement elements 162 and 164 of the watch band 150 can engage each other to secure the watch 100 to the wrist of the user 102. Securing and releasing the engagement elements 162 and 164 of the watch band 150 about an axis (e.g., through the wrist of the user 102) can change at least one characteristic (e.g., resistance) of at least a portion of the watch band 150 in a manner that is detectable.

In the relaxed off-wrist configuration, as shown in FIG. 4, the watch band 150 can have a first curvature, for example in which it is not wrapped around the wrist. In the secured on-wrist configuration, as shown in FIG. 5, the watch band 150 can have a second curvature, different (e.g., greater) than the first curvature, for example in which it is wrapped around the wrist (e.g., to below watch body 104). The bending of the watch band 150 about an axis (e.g., through the wrist of the user 102) can change at least one characteristic (e.g., resistance) of at least a portion of the watch band 150 in a manner that is detectable.

Figure 6:
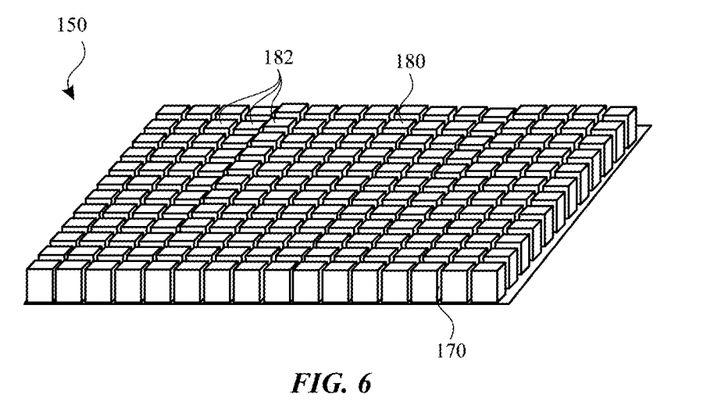
FIG. 6 illustrates a perspective view of a watch band in a relaxed configuration, according to some embodiments of the present disclosure.
Figure 7:
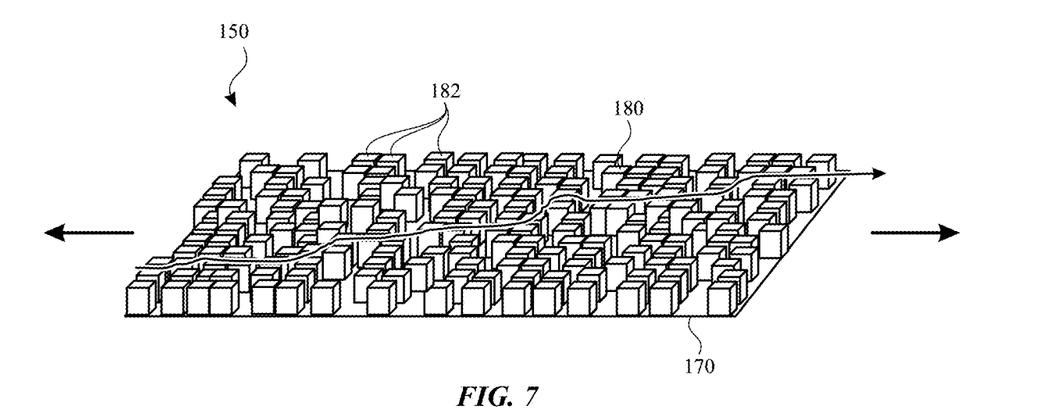
FIG. 7 illustrates a perspective view of the watch band of FIG. 6 in a stretched configuration, according to some embodiments of the present disclosure.
Figure 8:
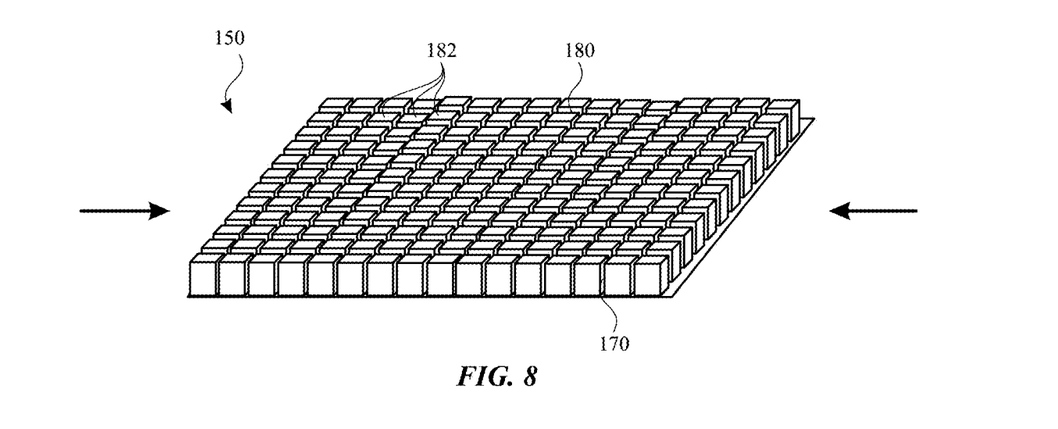
FIG. 8 illustrates a perspective view of the watch band of FIG. 7 in a relaxed configuration, according to some embodiments of the present disclosure.

Referring now to FIGS. 6-8, a watch band can facilitate a change to at least one characteristic (e.g., resistance) of at least a portion of the watch band when the watch band changes its configuration. The watch band 150 can include a substrate 170 and a conductive layer 180. The conductive layer 180 can include multiple segments 182 that are each independently coupled to the substrate 170 and moveable, separable, or otherwise adjustable relative to each other.

In some embodiments, the substrate 170 can be formed, at least in part, from a polymer, such as an elastomer, fluoroelastomeric polymer, FKM, or other polymer, such as those having a Shore durometer selected for having flexibility suitable for easily contouring to a user's wrists while maintaining sufficient stiffness to maintain support of the watch 100 when attached to the wrist of user 102. For example, bands of certain embodiments may have a Shore A durometer ranging from 60 to 80 and/or a tensile strength greater than 12 MPa. In some embodiments, a fluoroelastomeric polymer (or other suitable polymer) can be doped or treated with one or more other materials. For example, the polymer can be doped with an agent configured to provide the polymer with a selected color, odor, taste, hardness, elasticity, stiffness, reflectivity, refractive pattern, texture and so on. In other examples, the doping agent can confer other properties to the fluoroelastomeric polymer including, but not necessarily limited to, electrical conductivity and/or insulating properties, magnetic and/or diamagnetic properties, chemical resistance and/or reactivity properties, infrared and/or ultraviolet light absorption and/or reflectivity properties, visible light absorption and/or reflectivity properties, antimicrobial and/or antiviral properties, oleophobic and/or hydrophobic properties, thermal absorption properties, pest repellant properties, colorfast and/or anti-fade properties, deodorant properties, antistatic properties, medicinal properties, liquid exposure reactivity properties, low and/or high friction properties, hypoallergenic properties, and so on.

Some embodiments described herein include configurations in which the watch band 150 is formed, at least in part, from a non-compliant material into a compliant structure. For example, a metallic mesh can be used to form at least a portion of the watch band 150. In some embodiments, the watch band can be formed, at least in part, by joining a number of metal links. In some embodiments, the watch band can be formed, at least in part, by joining a number of glass or crystal links. In some embodiments, the watch band 150 can be formed form a combination of complaint and non-compliant materials.

The conductive layer 180 can be formed from a metal or other conductive material that is deposited on the substrate 170. For example, the conductive layer 180 can include copper, and/or another conductive metal or metal alloy. The conductive layer 180 can be initially formed as a continuous structure and subsequently separated into discrete segments 182 upon stretching, bending, or other movement of the substrate 170. Such movement can create cracks in the conductive layer 180 to define the segments 182 as discrete and separate parts from each other.

As shown in FIG. 6, in a first configuration, the watch band 150 can provide the substrate 170 in a state that corresponds to the watch band 150 in a relaxed, compressed, bent, or unbent state. For example, the first configuration can correspond to an on-wrist or off-wrist configuration. In the first configuration, the segments 182 of the conductive layer 180 can be relatively closer to each other than in other configurations. For example, adjacent pairs of the segments 182 can be in contact with each other or otherwise relatively closer to each other than in other configurations. While in the first configuration, a pathway through the conductive layer 180 and along the segments 182 can have a relatively lower resistance than in other configurations. Accordingly, a measured resistance across the conductive layer 180 can indicate to a detector that the watch band 150 is in the first configuration.

As shown in FIG. 7, in a second configuration, the watch band 150 can provide the substrate 170 in a state that corresponds to the watch band 150 in a relaxed, stretched, bent, or unbent state. For example, the second configuration can correspond to an on-wrist or off-wrist configuration. In the first configuration, the segments 182 of the conductive layer 180 can be relatively farther apart from each other than in other configurations. For example, adjacent pairs of the segments 182 can be separated, spaced apart or otherwise relatively farther apart from each other than in other configurations. While in the first configuration, a pathway through the conductive layer 180 and along the segments 182 can have a relatively higher resistance than in other configurations. Such a change in resistance can be due to the more tortuous pathway formed by the separated segments 182 and/or air gaps formed between the segments 182.

Accordingly, a measured resistance across the conductive layer 180 can indicate to a detector that the watch band 150 is in the second configuration.

As shown in FIG. 8, the watch band 150 can return to the first configuration following a duration of time in the second configuration. It will be understood that either the first configuration or the second configuration can correspond to the watch band 150 in a relaxed state. Accordingly, in some embodiments, the watch band 150 can return to the second configuration following a duration of time in the first configuration. It will be further understood that either the first configuration or the second configuration can correspond to the watch band 150 in a stretched, compressed, or bent state. It will be further understood that any number of other configurations can be provided and detected based on corresponding changes in the resistance across the conductive layer 180. For example, configurations can include any between and/or beyond either of the first configuration and the second configuration.

Figure 9:
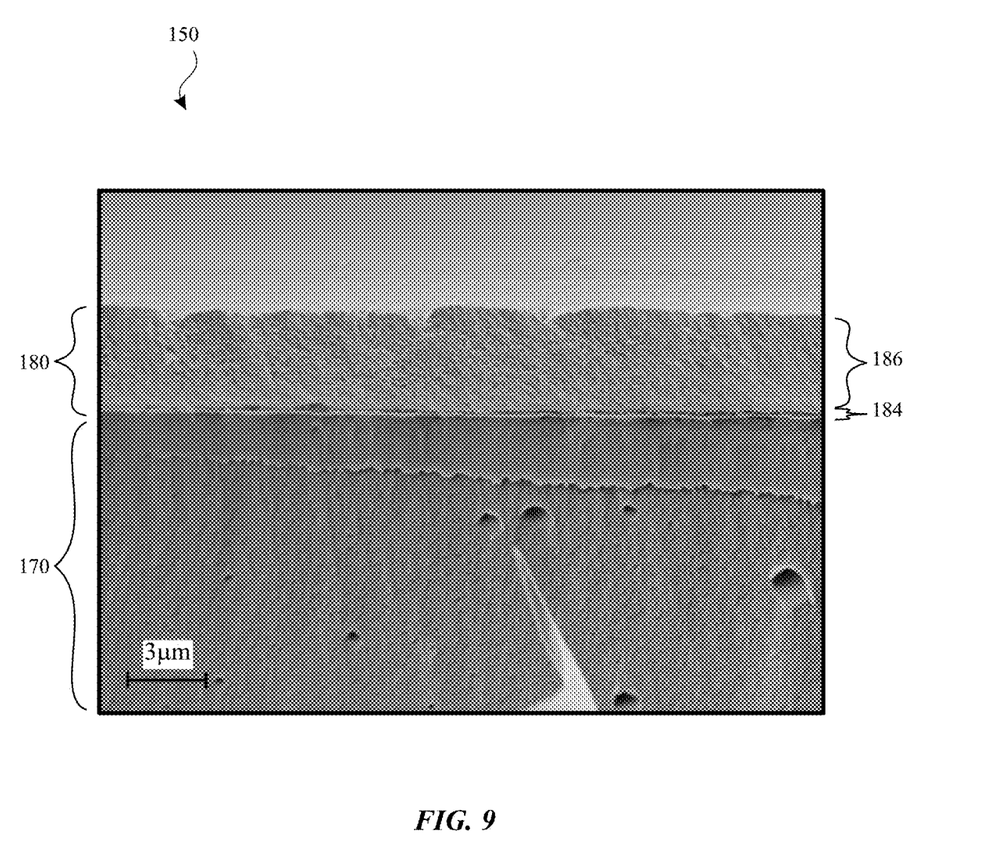
FIG. 9 shows an image of a cross-section of a watch band, according to some embodiments of the present disclosure.

Referring now to FIG. 9, a conductive layer can be deposed upon a substrate in a manner that facilitates durable coupling there between. FIG. 9 shows a cross-sectional view of a portion of a watch band 150, including a substrate 170. Upon the substrate 170, the conductive layer 180 can be formed by a first conductive layer 184 and a second conductive layer 186. For example, the second conductive layer 186 can be coupled to the substrate 170 by the first conductive layer 184.

The first conductive layer 184 and the second conductive layer 186 can be applied in sequence, by different mechanisms, and having different characteristics. For example, the first conductive layer 184 can be applied to the substrate 170, and thereafter the second conductive layer 186 can be applied to the first conductive layer 184.

The first conductive layer 184 can be applied by an electroless plating process. For example, the electroless plating process can omit usage of an electric current to bind the metal particles of the first conductive layer 184 onto the substrate 170. The electroless plating process can rely strictly on chemical reactions to bind metal particles onto the surface of the substrate 170. In the process, the substrate 170 can be cleaned and treated, for example with a catalytic solution to induce oxidation. The metal particles of the first conductive layer 184 then bind to the surface of the substrate 170. The use of electroless plating facilitates binding between the first conductive layer 184, which is conductive, and the substrate 170, which is not conductive. While the thickness of the first conductive layer 184 is thin relative to the second conductive layer 186, such thinness can facilitate cracking upon transitions of the substrate 170. For example, the first conductive layer 184 can be about 100, 200, 300, 400, or 500 nm thick.

The second conductive layer 186 can be applied by an electroplating process. For example, the electroplating process can include the use of an electric current to bind the metal particles of the second conductive layer 186 onto a surface of the first conductive layer 184. In the process, the first conductive layer 184 is cleaned and then submerged in a bath of the metal plating particles. An electric current is then applied to the first conductive layer 184, which causes the metal particles of the second conductive layer 186 to attach and bind to the surface of the first conductive layer 184. The electroplating process can provide and focus activity between the first conductive layer 184 and the second conductive layer 186, as such are both conductive. The thickness of the second conductive layer 186 can be substantially thicker relative to the first conductive layer 184. For example, the second conductive layer 186 can be about 1, 2, 3, 4, or 5 μm thick. By further example, the second conductive layer 186 can be about 2, 5, 10, 15, 20, or greater than 20 times thicker than the first conductive layer 184.

Figure 10:
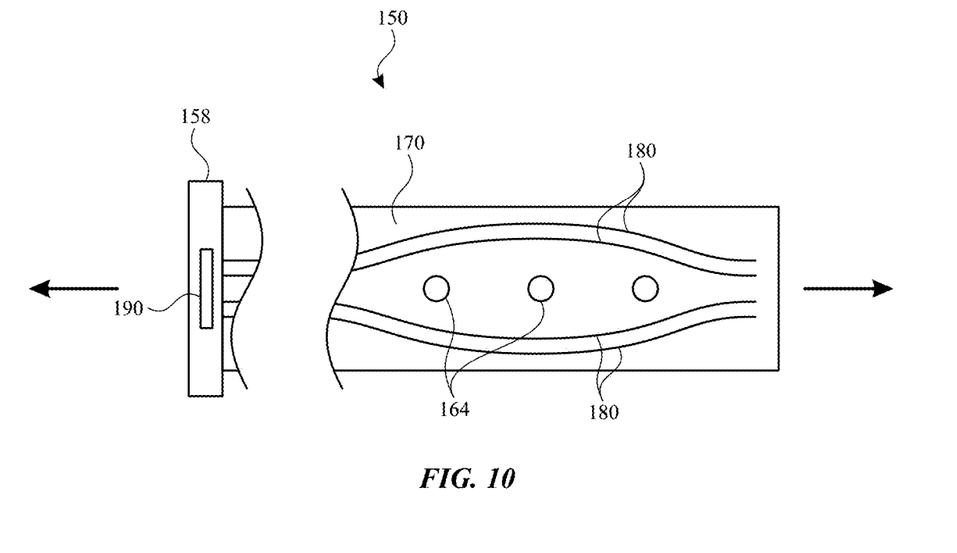
FIG. 10 illustrates a top view of a watch band, according to some embodiments of the present disclosure.

Referring now to FIG. 10, a watch band can facilitate a change to at least one characteristic (e.g., resistance) of at least a portion of the watch band when the watch band changes its length. As discussed above, in the relaxed off-wrist configuration, the watch band 150 can have a first length, and in the secured on-wrist configuration, the watch band 150 can have a second length, different (e.g., greater) than the first length.

The stretching of the watch band 150 along its length can change at least one characteristic (e.g., resistance) of at least a portion of the watch band 150 in a manner that is detectable. For example, the watch band 150 can include one or more conductive layers 180 that form traces extending along a surface of a substrate 170. The watch band 150 can include an attachment element 158 for engaging a watch body along with an interface 190 to connect a detector of the watch body with the conductive layers 180. As the watch band 150 stretches her compresses in length, the resistance along one or more of the conductive layers can change to indicate to the detector that the watch band 150 has changed its configuration and correspondingly changed its length. It will be understood that one or more of the conductive layers 180 can form a closed-loop such that the interface 190 and/or a detector can measure a resistance between the ends of the loop and along a pathway there through.

Figure 11:
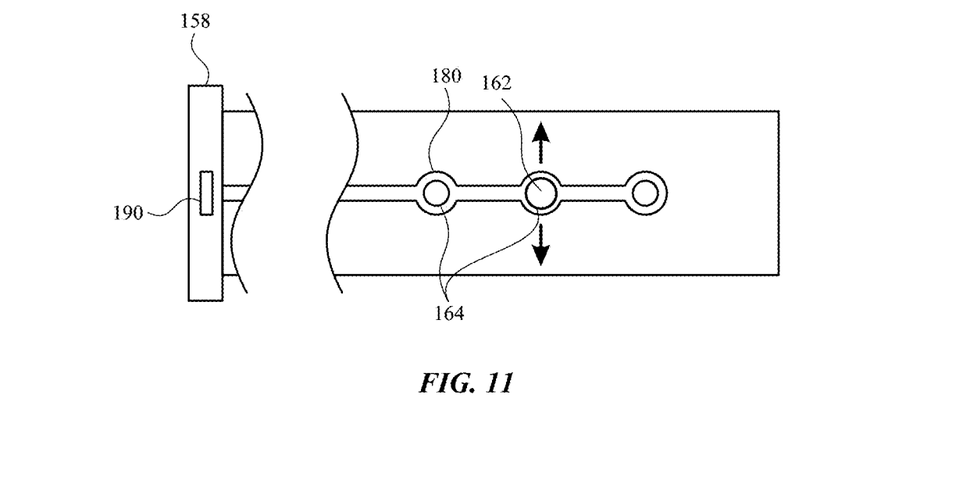
FIG. 11 illustrates a top view of a watch band, according to some embodiments of the present disclosure.

Referring now to FIG. 11, a watch band can facilitate a change to at least one characteristic (e.g., resistance) of at least a portion of the watch band when the watch band engages or disengages with its engagement elements. As discussed above, in the relaxed off-wrist configuration, the engagement elements 162 and 164 of the watch band 150 can be disengaged and/or separated from each other, and in the secured on-wrist configuration, the engagement elements 162 and 164 of the watch band 150 can engage each other to secure the watch 100 to the wrist of the user 102.

Securing and releasing the engagement elements 162 and 164 of the watch band 150 can change at least one characteristic (e.g., resistance) of at least a portion of the watch band 150 in a manner that is detectable. For example, the watch band 150 can include one or more conductive layers 180 that form traces near or around one or more of the engagement elements formed by or near the substrate 170. As the engagement elements 162 and 164 engage each other, the substrate 170 can be stretched or compressed to produce a change in the resistance along one or more of the conductive layers 180. Such a change can indicate to the detector that the watch band 150 has changed been engaged or disengaged. By further example, different conductive layers 180 can detect engagement by different engagement elements 162 and 164, so that a specific configuration can be detected. It will be understood that one or more of the conductive layers 180 can form a closed-loop such that the interface 190 and/or a detector can measure a resistance between the ends of the loop and along a pathway there through.

Referring now to FIG. 12-17, a watch band can facilitate a change to at least one characteristic (e.g., resistance) of at least a portion of the watch band when the watch band changes its curvature. In the relaxed off-wrist configuration the watch band 150 can have a first curvature, and in the secured on-wrist configuration, the watch band 150 can have a second curvature.

Figure 12:
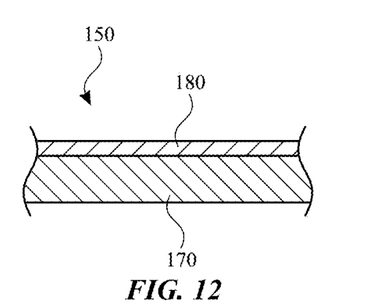
FIG. 12 illustrates a side sectional view of a watch band in a relaxed configuration, according to some embodiments of the present disclosure.
Figure 13:
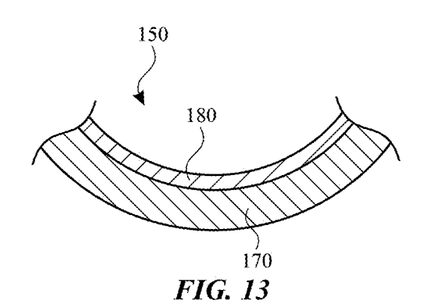
FIG. 13 illustrates a side sectional view of the watch band of FIG. 12 in a curved configuration, according to some embodiments of the present disclosure.

The bending of the watch band 150 about an axis can change at least one characteristic (e.g., resistance) of at least a portion of the watch band 150 in a manner that is detectable. For example, as shown in FIGS. 12 and 13, the bending of the substrate 170 from a first curvature to a second curvature can compress the conductive layer 180 where it is positioned on an inner (e.g., concave) side of the substrate 170. Accordingly, the conductive layer 180 can demonstrate a decrease in resistance as the segments of the conductive layer 180 are pressed together to form more efficient conductive pathways.

Figure 14:
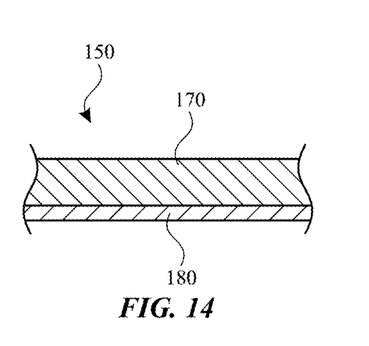
FIG. 14 illustrates a side sectional view of a watch band in a relaxed configuration, according to some embodiments of the present disclosure.
Figure 15:
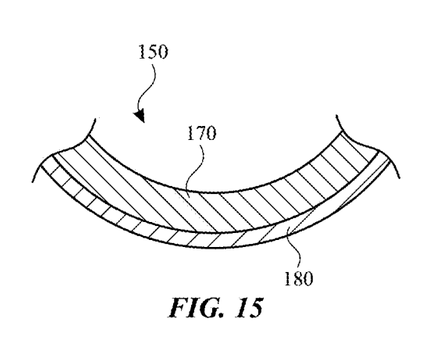
FIG. 15 illustrates a side sectional view of the watch band of FIG. 14 in a curved configuration, according to some embodiments of the present disclosure.

By further example, as shown in FIGS. 14 and 15, the bending of the substrate 170 from a first curvature to a second curvature can stretch the conductive layer 180 where it is positioned on an outer (e.g., convex) side of the substrate 170. Accordingly, the conductive layer 180 can demonstrate an increase in resistance as the segments of the conductive layer 180 are separated from each other to form less efficient conductive pathways.

Figure 16:
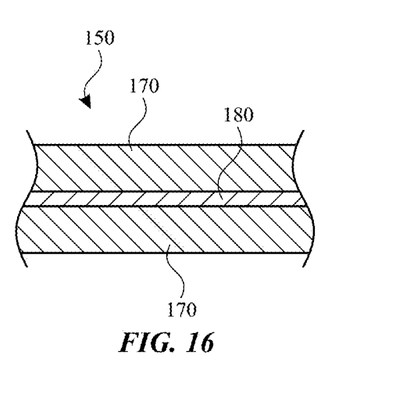
FIG. 16 illustrates a side sectional view of a watch band in a relaxed configuration, according to some embodiments of the present disclosure.
Figure 17:
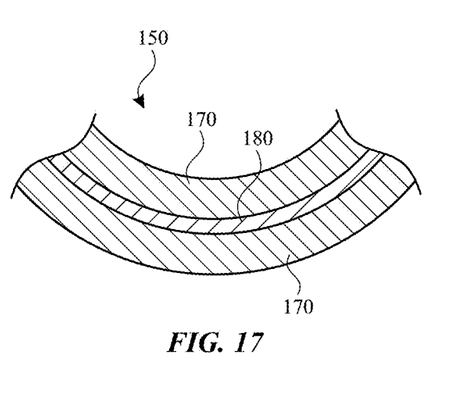
FIG. 17 illustrates a side sectional view of the watch band of FIG. 16 in a curved configuration, according to some embodiments of the present disclosure.

By further example, as shown in FIGS. 16 and 17, the bending of the substrate 170 from a first curvature to a second curvature can have less pronounced or an overall negligible effect on the resistance of the conductive layer 180. Where the conductive layer 180 is positioned between opposing layers of the substrate 170, the conductive layer 180 can demonstrate nominal or no increase or decrease in resistance when bent in either direction as the segments of the conductive layer 180 are maintained in a generally consistent configuration. It will be understood that such a conductive layer can nonetheless be used to detect changes in resistance to longitudinal stretching, compression, or other movements.

The watch 100 can perform an action that has been determined to be associated with the detected characteristic (e.g., resistance). For example, the action corresponding to the detected characteristic can include instructions for execution by the processor 206 and/or other components of the watch 100. Alternatively or additionally, the action can include causing another device, apart from the electronic device 100, to execute instructions. The action can be performed automatically upon detection of the characteristic. Additionally or alternatively, the watch 100 can provide a prompt requesting user confirmation of the action, and the action can be performed after user confirmation is received. Additionally or alternatively, a user can manually override or modify the action.

Various exemplary actions are discussed below. Actions performed by the watch 100 in response to detection of a characteristic include influencing regular operation of the watch 100. For example, the regular operation of the watch 100 can be maintained with additional or altered features based on the detected characteristic. As such, the user's experience with the watch 100 during its regular operation is enhanced.

In some embodiments, upon detection of a characteristic, the watch 100 provides a feature of a visual user interface that corresponds to a characteristic of the band 110.

In some embodiments, upon detection of a characteristic, other settings of the watch 100 can be modified. A band in a given configuration can be associated with an activity that is supported by the watch 100. For example, the watch 100 can display particular information, track activity of the user, take a biometric reading, record a location of the user, launch an activity tracking app, and/or modify notifications settings (e.g., to be more prominent).

Actions performed by the watch 100 in response to detection of a characteristic include actions outside of the regular operation of the watch 100. For example, the watch 100 can perform actions that are only available when a band is detected to be in a particular configuration.

In some embodiments, a detection of a characteristic can serve as authorization for otherwise unavailable actions. For example, the watch can be locked when in an off-wrist configuration. By further example, the watch can be unlocked or unlockable when in an on-wrist configuration.

In some embodiments, the watch 100 can perform detections and take actions in a manner that is not necessarily perceivable by a user. For example, a watch 100 can track usage of one or more bands and the configurations thereof. The tracked usage information includes dates, times, durations, locations, activities, biometrics of the user, and/or environmental features in relation to periods before, during, and/or after usage of each band. The tracked usage information can be collected during a background process of the watch 100. The tracked usage information can be output to a user or uploaded to an external device for analysis. The tracked usage information can be used for machine learning in relation to how each band is used.

The watch 100 can perform a variety of other actions upon identification of a band 150. It will be recognized that the detection of a characteristic can be followed by any associated action that can be performed by the watch 100. For example, where the watch 100 has the required capabilities, the watch 100 launches an app, opens a website, starts a timer, displays a message, provides an alert, communicates with another device, and/or other functions.

Accordingly, watch bands described herein can facilitate a watch's ability to perform one or more operations based on the detected characteristic and configuration of the watch band. Characteristics of the watch band can change when placed in different configurations, and each of these characteristics can be correlated with each of the various configurations. The characteristics can be measured to detect in which of the various configurations the watch band is in. For example, the watch band can include a conductive trace that changes its resistance when the watch band changes its configuration. For example, the resistance can change based on stretching of the watch band, bending of the watch band, and/or securement and release of an engagement element.

Various examples of aspects of the disclosure are described below as clauses for convenience. These are provided as examples, and do not limit the subject technology.

Clause A: a watch comprising: a watch body comprising: a detector; and a watch and configured to be coupled to the watch body and comprising: a substrate of an elastic material; and a conductive layer comprising conductive segments extending along a surface of the substrate and configured to move relative to each other as the substrate stretches, wherein the detector of the watch body is configured to: measure a resistance along a path through the conductive segments; and perform an operation based on the resistance.

Clause B: a watch band comprising: a substrate configured to transition between a first configuration in which the substrate defines a first dimension and a second configuration in which the substrate defines a second dimension, different than the first dimension; a conductive layer configured to provide a first resistance while the substrate is in the first configuration and a second resistance, different than the first resistance, while the substrate is in the second configuration.

Clause C: a watch comprising: a watch band comprising: a substrate configured to stretch in at least one dimension; a first conductive layer; and a second conductive layer coupled to the substrate by the first conductive layer, wherein the second conductive layer is thicker than the first conductive layer; and a watch body comprising a detector configured to measure a resistance along a path through first conductive layer and the second conductive layer.

One or more of the above clauses can include one or more of the features described below. It is noted that any of the following clauses may be combined in any combination with each other, and placed into a respective independent clause, e.g., clause A, B, or C.

Clause 1: the detector is further configured to detect, based on the resistance, whether the watch band is securing the watch to a wrist of a user.

Clause 2: the detector detects, based on the resistance, that the watch band is not securing the watch to the wrist of the user, the detector is further configured to prevent access to at least one function of the watch until a passcode is provided.

Clause 3: the detector is further configured to detect, based on the resistance, a size of a wrist of a user.

Clause 4: the detector is further configured to detect, based on the resistance, a movement of a user wearing the watch.

Clause 5: the detector is further configured to detect, based on the resistance, a blood pressure of a user wearing the watch.

Clause 6: the first configuration is achieved when the watch band is securing a watch to a wrist of a user; and the second configuration is achieved when the watch is removed from the wrist of the user.

Clause 7: the first dimension is a length of the substrate in a relaxed configuration; and the second dimension is a length of the substrate in a stretched configuration.

Clause 8: in the first configuration, the substrate has a first curvature; and in the second configuration, the substrate has a second curvature, different than the first curvature.

Clause 9: the conductive layer is positioned on an inner surface of the substrate, such that the conductive layer is facing toward a wrist of a user and placed under compressing when the watch band is applied to the wrist of the user.

Clause 10: the conductive layer is positioned on an outer surface of the substrate, such that the conductive layer is facing away from a wrist of a user and placed under tension when the watch band is applied to the wrist of the user.

Clause 11: the watch band further comprises: a first band portion having a first engagement element; and a second band portion having a second engagement element; in the first configuration, the first engagement element engages the second engagement element; and in the second configuration, the first engagement element does not engage the second engagement element.

Clause 12: the first engagement element comprises a post; the second engagement element comprises an opening extending through the substrate and configured to receive the post; and the conductive layer extends about at least a portion of the opening.

Clause 13: the substrate comprises a non-conductive polymer.

Clause 14: the second conductive layer is between 5 and 15 times thicker than the first conductive layer.

Clause 15: the first conductive layer is between 100 and 500 nm thick; and the second conductive layer is between 1 and 5 µm thick.

Clause 16: the second conductive layer comprises conductive segments configured to move relative to each other as the substrate stretches.

Clause 17: the first conductive layer and the second conductive layer comprise copper.

As described above, one aspect of the present technology may include the gathering and use of data available from various sources. The present disclosure contemplates that in some instances, this gathered data may include personal information data that uniquely identifies or can be used to contact or locate a specific person. Such personal information data can include demographic data, location-based data, telephone numbers, email addresses, twitter ID's, home addresses, data or records relating to a user's health or level of fitness (e.g., vital signs measurements, medication information, exercise information), date of birth, or any other identifying or personal information.

The present disclosure recognizes that the use of such personal information data, in the present technology, can be used to the benefit of users. For instance, health and fitness data may be used to provide insights into a user's general wellness, or may be used as positive feedback to individuals using technology to pursue wellness goals.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the US, collection of or access to certain health data may be governed by federal and/or state laws, such as the Health Insurance Portability and Accountability Act (HIPAA); whereas health data in other countries may be subject to other regulations and policies and should be handled accordingly. Hence different privacy practices should be maintained for different personal data types in each country.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of advertisement delivery services, the present technology can be configured to allow users to select to "opt in" or "opt out" of participation in the collection of personal information data during registration for services or anytime thereafter. In another example, users can select not to provide mood-associated data for targeted content delivery services. In yet another example, users can select to limit the length of time mood-associated data is maintained or entirely prohibit the development of a baseline mood profile. In addition to providing "opt in" and "opt out" options, the present disclosure contemplates providing notifications relating to the access or use of personal information. For instance, a user may be notified upon downloading an app that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing specific identifiers (e.g., date of birth, etc.), controlling the amount or specificity of data stored (e.g., collecting location data a city level rather than at an address level), controlling how data is stored (e.g., aggregating data across users), and/or other methods.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, content can be selected and delivered to users by inferring preferences based on non-personal information data or a bare minimum amount of personal information, such as the content being requested by the device associated with a user, other non-personal information available to the content delivery services, or publicly available information.

A reference to an element in the singular is not intended to mean one and only one unless specifically so stated, but rather one or more. For example, "a" module may refer to one or more modules. An element proceeded by "a," "an," "the," or "said" does not, without further constraints, preclude the existence of additional same elements.

Headings and subheadings, if any, are used for convenience only and do not limit the invention. The word exemplary is used to mean serving as an example or illustration. To the extent that the term include, have, or the like is used, such term is intended to be inclusive in a manner similar to the term comprise as comprise is interpreted when employed as a transitional word in a claim. Relational terms such as first and second and the like may be used to distinguish one entity or action from another without necessarily requiring or implying any actual such relationship or order between such entities or actions.

Phrases such as an aspect, the aspect, another aspect, some aspects, one or more aspects, an implementation, the implementation, another implementation, some implementations, one or more implementations, an embodiment, the embodiment, another embodiment, some embodiments, one or more embodiments, a configuration, the configuration, another configuration, some configurations, one or more configurations, the subject technology, the disclosure, the present disclosure, other variations thereof and alike are for convenience and do not imply that a disclosure relating to such phrase(s) is essential to the subject technology or that such disclosure applies to all configurations of the subject technology. A disclosure relating to such phrase(s) may apply to all configurations, or one or more configurations. A disclosure relating to such phrase(s) may provide one or more examples. A phrase such as an aspect or some aspects may refer to one or more aspects and vice versa, and this applies similarly to other foregoing phrases.

A phrase "at least one of" preceding a series of items, with the terms "and" or "or" to separate any of the items, modifies the list as a whole, rather than each member of the list. The phrase "at least one of" does not require selection of at least one item; rather, the phrase allows a meaning that includes at least one of any one of the items, and/or at least one of any combination of the items, and/or at least one of each of the items. By way of example, each of the phrases "at least one of A, B, and C" or "at least one of A, B, or C" refers to only A, only B, or only C; any combination of A, B, and C; and/or at least one of each of A, B, and C.

It is understood that the specific order or hierarchy of steps, operations, or processes disclosed is an illustration of exemplary approaches. Unless explicitly stated otherwise, it is understood that the specific order or hierarchy of steps, operations, or processes may be performed in different order. Some of the steps, operations, or processes may be performed simultaneously. The accompanying method claims, if any, present elements of the various steps, operations or processes in a sample order, and are not meant to be limited to the specific order or hierarchy presented. These may be performed in serial, linearly, in parallel or in different order. It should be understood that the described instructions, operations, and systems can generally be integrated together in a single software/hardware product or packaged into multiple software/hardware products.

In one aspect, a term coupled or the like may refer to being directly coupled. In another aspect, a term coupled or the like may refer to being indirectly coupled.

Terms such as top, bottom, front, rear, side, horizontal, vertical, and the like refer to an arbitrary frame of reference, rather than to the ordinary gravitational frame of reference. Thus, such a term may extend upwardly, downwardly, diagonally, or horizontally in a gravitational frame of reference.

The disclosure is provided to enable any person skilled in the art to practice the various aspects described herein. In some instances, well-known structures and components are shown in block diagram form in order to avoid obscuring the concepts of the subject technology. The disclosure provides various examples of the subject technology, and the subject technology is not limited to these examples. Various modifications to these aspects will be readily apparent to those skilled in the art, and the principles described herein may be applied to other aspects.

All structural and functional equivalents to the elements of the various aspects described throughout the disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for".

The title, background, brief description of the drawings, abstract, and drawings are hereby incorporated into the disclosure and are provided as illustrative examples of the disclosure, not as restrictive descriptions. It is submitted with the understanding that they will not be used to limit the scope or meaning of the claims. In addition, in the detailed description, it can be seen that the description provides illustrative examples and the various features are grouped together in various implementations for the purpose of streamlining the disclosure. The method of disclosure is not to be interpreted as reflecting an intention that the claimed subject matter requires more features than are expressly recited in each claim. Rather, as the claims reflect, inventive subject matter lies in less than all features of a single disclosed configuration or operation. The claims are hereby incorporated into the detailed description, with each claim standing on its own as a separately claimed subject matter.

The claims are not intended to be limited to the aspects described herein, but are to be accorded the full scope consistent with the language of the claims and to encompass all legal equivalents. Notwithstanding, none of the claims are intended to embrace subject matter that fails to satisfy the requirements of the applicable patent law, nor should they be interpreted in such a way.

What is claimed is:

1. A watch comprising:
   a watch body comprising:
      a detector; and
   a watch band configured to be coupled to the watch body and comprising:
      a substrate of an elastic material defining an opening configured to stretch to engage a post; and
      a conductive layer comprising conductive segments extending along a surface of the substrate and configured to move relative to each other and change a resistance along a path through the conductive segments as the opening of the substrate stretches and engages the post,
   wherein the detector of the watch body is configured to:
      measure the resistance along the path through the conductive segments; and
      perform an operation based on the resistance.

2. The watch of claim 1, wherein the detector is further configured to detect, based on the resistance, whether the watch band is securing the watch to a wrist of a user.

3. The watch of claim 2, wherein the detector detects, based on the resistance, that the watch band is not securing the watch to the wrist of the user, the detector is further configured to prevent access to at least one function of the watch until a passcode is provided.

4. The watch of claim 1, wherein the detector is further configured to detect, based on the resistance, a size of a wrist of a user.

5. The watch of claim 1, wherein the detector is further configured to detect, based on the resistance, a movement of a user wearing the watch.

6. The watch of claim 1, wherein the detector is further configured to detect, based on the resistance, a blood pressure of a user wearing the watch.

7. A watch band comprising:
   a first band portion having a first engagement element;
   a second band portion having a second engagement element;
   a substrate configured to transition between a first configuration in which the first engagement element engages the second engagement element and a second configuration in which the first engagement element does not engage the second engagement element; and
   a conductive layer configured to provide a first resistance while the substrate is in the first configuration and a second resistance, different than the first resistance, while the substrate is in the second configuration.

8. The watch band of claim 7, wherein:
   the first configuration is achieved when the watch band is securing a watch to a wrist of a user; and
   the second configuration is achieved when the watch is removed from the wrist of the user.

9. The watch band of claim 7, wherein:
   the substrate defines a first dimension that is a first length of the substrate in a relaxed configuration; and
   the substrate defines a second dimension that is a second length of the substrate in a stretched configuration.

10. The watch band of claim 7, wherein:
    in the first configuration, the substrate has a first curvature; and
    in the second configuration, the substrate has a second curvature, different than the first curvature.

11. The watch band of claim 10, wherein the conductive layer is positioned on an inner surface of the substrate, such that the conductive layer is facing toward a wrist of a user and placed under compressing when the watch band is applied to the wrist of the user.

12. The watch band of claim 10, wherein the conductive layer is positioned on an outer surface of the substrate, such that the conductive layer is facing away from a wrist of a user and placed under tension when the watch band is applied to the wrist of the user.

13. The watch band of claim 7, wherein:
    the first engagement element comprises a post;
    the second engagement element comprises an opening extending through the substrate and configured to receive the post; and
    the conductive layer extends about at least a portion of the opening.

14. A watch comprising:
    a watch band comprising:
       a substrate configured to stretch in at least one dimension;
       a first conductive layer; and
       a second conductive layer coupled to the substrate by the first conductive layer, wherein the second conductive layer is thicker than the first conductive layer in a direction of an axis that extends through the first conductive layer and the second conductive layer; and
    a watch body comprising a detector configured to measure a resistance along a path through first conductive layer and the second conductive layer.

15. The watch of claim 14, wherein the substrate comprises a non-conductive polymer.

16. The watch of claim 14, wherein the second conductive layer is between 5 and 15 times thicker than the first conductive layer.

17. The watch of claim 14, wherein:
    the first conductive layer is between 100 and 500 nm thick; and
    the second conductive layer is between 1 and 5 µm thick.

18. The watch of claim 14, wherein the second conductive layer comprises conductive segments configured to move relative to each other as the substrate stretches.

19. The watch of claim 14, wherein the first conductive layer and the second conductive layer comprise copper.

* * * * *